United States Patent [19]
Li et al.

[11] Patent Number: 5,942,414
[45] Date of Patent: *Aug. 24, 1999

[54] POLYNUCLEOTIDES ENCODING HUMAN G-PROTEIN COUPLED RECEPTOR HIBEF51

[75] Inventors: Yi Li, Gaithersburg; Mark D. Adams, North Potomac, both of Md.

[73] Assignee: Human Genome Sciences, Inc., Rockville, Md.

[*] Notice: This patent issued on a continued prosecution application filed under 37 CFR 1.53(d), and is subject to the twenty year patent term provisions of 35 U.S.C. 154(a)(2).

[21] Appl. No.: 08/465,971

[22] Filed: Jun. 6, 1995

[51] Int. Cl.$^6$ .......................... C12N 15/12; C07K 14/705
[52] U.S. Cl. ................ 435/69.1; 435/252.3; 435/254.11; 435/320.1; 435/325; 536/23.5
[58] Field of Search ................................ 535/23.5, 24.31; 435/69.1, 325, 252.3, 254.11, 320.1

[56] References Cited

PUBLICATIONS

Ross, P.C. et al., Proc. Of the National Academy of Science, 87:3052–3056 (1990).
Libert, F. et al., Science, 244:569–572 (1989).
Eva, C. et al., FEBS Letters, 271:81–84 (1990).
Hla, T. et al., The Journal of Biol. Chemistry, 265 (16):9308–9313 (1990).
Meyerhof, W. et al., FEBS Letters, 284(2):155–160 (1991).
Pepperl, D.J. et al., CRC Press, 45–46 (1994).
Fraser et al., J. of Biol. Chem., vol. 264, 11754–11761, Jul. 15, 1989.

*Primary Examiner*—Sally P. Teng
*Attorney, Agent, or Firm*—Kenley K. Hoover

[57] ABSTRACT

Human G-protein Coupled receptor HIBEF51 polypeptides and DNA (RNA) encoding such polypeptides and a procedure for producing such polypeptides by recombinant techniques is disclosed. Also disclosed are methods for utilizing such polypeptides for identifying antagonists and agonists to such polypeptides and methods of using the agonists and antagonists therapeutically to treat conditions related to the underexpression and overexpression of the receptor polypeptides, respectively. Also disclosed are diagnostic methods for detecting a mutation in the human G-protein Coupled receptor HIBEF51 nucleic acid sequences and detecting a level of the soluble form of the receptors in a sample derived from a host.

20 Claims, 7 Drawing Sheets

FIG. 1A

```
         10                30                50
AATTACAGGTAACATTCTGAAATTGAACTAAACAGTAAATTCTGTTGAAATGTTTCAAA
         70                90               110
GAGGCAAATATATATTGGAATCAATGAAGAAGTAAATTATCTTGGCTAATTTTATTA
        130               150               170
GTGGTAAATTGTAGTGAAAGGTTTTCCTAAATATTATAAGCAAATTCCTTTTCTCCCCGT
        190               210               230
CTCAAATGAAAGGAAATGGGGTAAATTAATCTGACTGTGATTGGTTTGTTTATGCTG
        250               270               290
ATCTTGAAAGCTTGATGTTGCTGCTGCCTCCTCATACAGTACAGATCAGTTGTGTGGGGTG
        310               330               350
CTATTGAGGGTAGCCGTGAATAGTGGTGCCAGTAGGGTGGAGCGGGAGGATGATGCCA
        370               390               410
GCCTGAGCTAGCCAGGTTCTTTGATTAGGGCATTGGATGTGAAATGTAAAATGCTCTC
        430               450               470
CTTTTCTTCTATCAGCTGTTCAGAGGAGACTCATTACAACTCCCTGCTGAAGCTCCTAATC
        490               510               530
TTCTTCCCTTCTCTTCTACCCTTTCCCCTACCCCTCACTTGGCCTGAAGACGTTCTCCCC
        550               570               590
AGAGTTTACCTTGCTCCCCTGGTGCTATGTGTATGGTGAACCTGGCACTATGGCCGCGTC
        610               630               650
TGGGACTGGCCAGACAACTGCTGCTGGCTCTCCCTTATTCCAGGAAGGATTAAAGGGGAA
        670               690               710
TTGCACTGCAGGCAATGCCACCAGAGCAGCAGCCATCAGGAGCTTGGGAGTAAGGCTCCTC
        730               750               770
TGGCATTATTACACACATGCAAAGCTGACCGCAATGACAGCAGCTGCTTCTTTGAACTGT
```

MATCH WITH FIG. 1B

FIG. 1B

MATCH WITH FIG. 1A
```
        790                810                830
TGGCAGCAGCCAAGCGGCAGCATGAAGTGACAGATCACTCCTGAGCTCAAGATGAACTCC
                                                   M  N  S
        850                870                890
ACCTTGGATGGTAATCAGAGCAGCCACCCCTTTTGCCTTCTTGGCATTTGGCTATTTGGAA
 T  L  D  G  N  Q  S  S  H  P  F  C  L  L  A  F  G  Y  L  E
        910                930                950
ACTGTCAATTTTTGCCTTTTGGAAGTATTGATTATTGTCTTTCTAACTGTATTGATTATT
 T  V  N  F  C  L  L  E  V  L  I  I  V  F  L  T  V  L  I  I
        970                990               1010
TCTGGCAACATCATTGTGATTTTTGTATTTCACTGTGCACCTTTGTTGAACCATCACACT
 S  G  N  I  I  V  I  F  V  F  H  C  A  P  L  L  N  H  H  T
       1030               1050               1070
ACAAGTTATTTTATCCAGACTATGGCATATGCTGACCTTTTTGTTGGGGTGAGCTGCGTG
 T  S  Y  F  I  Q  T  M  A  Y  A  D  L  F  V  G  V  S  C  V
       1090               1110               1130
GTCCCTTCTTTATCACTCCTCCATCACCCCCTTCCAGTAGAGGAGTCCTTGACTTGCCAG
 V  P  S  L  S  L  L  H  H  P  L  P  V  E  E  S  L  T  C  Q
       1150               1170               1190
ATATTGGTTTTGTAGTATCAGTTCTGAAGAGCGTCTCCATGGCTTCTCTGGCCTGTATC
 I  F  G  F  V  V  S  V  L  K  S  V  S  M  A  S  L  A  C  I
       1210               1230               1250
AGCATTGATAGATACATTGCCATTACTAAACCTTTAACCTATAATACTCTGGTTACACCC
 S  I  D  R  Y  I  A  I  T  K  P  L  T  Y  N  T  L  V  T  P
       1270               1290               1310
TGGAGACTACGCCCTGTGTATTTCCTGATTTGGCTATACTCGACCCTGGTCTTCCTGCCT
 W  R  L  R  L  C  I  F  L  I  W  L  Y  S  T  L  V  F  L  P
```

MATCH WITH FIG. 1C

FIG. 1C

MATCH WITH FIG. 1B

```
                          1330                                 1350                                 1370
TCCTTTTTCCACTGGGGCAAACCTGGATATCATGGAGATGTGTTCAGTGGTGTGTGCGGAG
 S  F  F  H  W  G  K  P  G  Y  H  G  D  V  F  Q  W  C  A  E
                          1390                                 1410                                 1430
TCCTGGCACACCGACTCCTACTTCACCCTGTTCATCGTGATGATGTTATATGCCCCAGCA
 S  W  H  T  D  S  Y  F  T  L  F  I  V  M  M  L  Y  A  P  A
                          1450                                 1470                                 1490
GCCCTTATTGTCTGCTTCACCTATTCAACATCTTCCGCATCTGCCAACAGCACACAAAG
 A  L  I  V  C  F  T  Y  F  N  I  F  R  I  C  Q  Q  H  T  K
                          1510                                 1530                                 1550
GATATCAGCGAAAGGCAAGCCCGCTTCAGCAGCCAGAGTGGGGAGACTGGGGAAGTGCAG
 D  I  S  E  R  Q  A  R  F  S  S  Q  S  G  E  T  G  E  V  Q
                          1570                                 1590                                 1610
GCCTGTCCTGATAAGCGCTATGCCATGGTCCTGTTTCGAATCACTAGTGTATTTTACATC
 A  C  P  D  K  R  Y  A  M  V  L  F  R  I  T  S  V  F  Y  I
                          1630                                 1650                                 1670
CTCTGGTTGCCATATATCATCTACTTCTTGTTGGAAAGCTCCACTGGCCACAGCAACCGC
 L  W  L  P  Y  I  I  Y  F  L  L  E  S  S  T  G  H  S  N  R
                          1690                                 1710                                 1730
TTCGCATCCTTCTTGACCACCTGGCTTGCTATTAGTAACAGTTTCTGCAACTGTGTAATT
 F  A  S  F  L  T  T  W  L  A  I  S  N  S  F  C  N  C  V  I
                          1750                                 1770                                 1790
TATAGTCTCTCCAACAGTGTATTCCAAAGAGGACTAAAGCGCCTCTCAGGGCtATGTGT
 Y  S  L  S  N  S  V  F  Q  R  G  L  K  R  L  S  G  A  M  C
                          1810                                 1830                                 1850
ACTTCTTGTGCAAGTCAGACTACAGCCAACGACCCTTACACAGTTAGAAGCAAAGGCCCT
```

MATCH WITH FIG. 1D

FIG. 1D

MATCH WITH FIG. 1C

```
 T  S  C  A  S  Q  T  T  A  N  D  P  Y  T  V  R  S  K  G  P
CTTAATGGATGTCATATCTGAAGTGGCTCAGTTACGGGGTTCCCGTGTGTGTGTGT
              1870              1890              1910
 L  N  G  C  H  I  *
GTGTGTGTGTGTGTGTGTATTTTATCTCTAAGTATTCACTAGGAAATCTGGGA
              1930              1950              1970
CAGAATACTTTGACTCTAAACAATAGCATACAAATTATTCGTATGGATACCTTCTAAGTT
              1990              2010              2030
TGTAGAAATGGTTTCCCAAGTGCTTGTGAATTAGAAGACTCAAGATCATGAAGACAAAT
              2050              2070              2090
TGCTCTTGCTCTCAATTTTGAAATGTCTTGGAAATGACTACAGTTCTCAGATTTAAAAT
              2110              2130              2150
GAATAAAGCCATATCTAACTCACTCTTTGTCACTTTCTGGGCTCTTTCCAGCTATTT
              2170              2190              2210
CGTCAGCATTTAAAAAGTCATCACTCTTCTTGTCACTTTCTGGGCTCTTTCCAGCTATTT
              2230              2250              2270
GGGCCGTCATATGCAATTGATTTCTTCTAACGGAATAGTAAAATATAAATGAAAAGGTTTT
              2290              2310              2330
AGAATTACTTTTATGTATGCCAAAGCATAACTACACTGCAAGTTTCAACACTGTCATT
              2350              2370              2390
```

FIG. 1E

MATCH WITH FIG. 1D

```
       2410             2430             2450
TAGAAAGCCAAATGTTCTGTGTTTTATTCTCTTGAGAGAATTCTCAGTAGGGTGAATAAT
       2470             2490             2510
GTGAACACATAAACATTAATTTTAGAATTTTACAGTGAACCATGAAGCAAAAGTGCAATC
       2530             2550             2570
AAATTATACAATTTATGAAAAACTGAGCTACTTTTTGTGCCATGCTTCACAGAGATCTAA
       2590             2610             2630
AGATATGTGTGCGTAGAAGTAATCGTGTAGTACTTTTGCCCATGCCTTTGTGTTATGTCT
       2650             2670             2690
ATATTTAGAATATCTGAATTGTTAGATTTCTCTTTACAGCAAAATGTGCTTAAGCTAAA
       2710             2730             2750
AAGTAATTCAGGGAATTCGATATCAAGCTTATCGATACCGTCGACCTCGAGGGGGGCCC

GGTA
```

```
  1 MNSTL.DGNQSSHPFCLLAFGYLETVNFCLLEVLIIV....FLTVLIISG  45
    |.|  |::...|  .::.|| .:.|  .|.:|  .|.:
  1 MGSLQPDAGNASWNGTEAPGGARATPYSLQVTLTLVCLAGLLMLLTVFG  50

46 NIIVIFVFHCAPLLNHHTTSYFIQTMAYADLFVGVSCVVPSLLHHPLP   95
    |::||  .:  .:  ::|||:  :|  :||  :|  :::.
 51 NVLVIIAVFTSRALKAPQNLFLV.SLASADILVA..TLVIPFSLANEVMG 97

96 ..VEESLTCQIFGFVVSVLKSVSMASLACISIDRYIAITKPLTYNTLVTP 143
       :|:  :|  :::.|  :||:::|||  ||:::|  ||
 98 YWYFGKAWCEIYLALDVLFCTSSIVHLCAISLDRYWSITQAIEYNLKRTP 147

144 WRLRLCIFLIWLYSTLVFLPSFFHWGKPGYHGDVFQWCAESW...HTDSY 190
    :|:.|:.|.||  ||.|:..|.  |:.  |:  ::  :.:
148 RRIKAIIITVWWVISAVISFPPLISIEKKG..GGGGPQPAEPRCEINDQKW 195

191 FTLFIVMMLYAPAALIVCFTYFNIFRICQQHTKDISER........... 228
```

FIG. 2A

MATCH WITH FIG. 2B

FIG. 2B

MATCH WITH FIG. 2A

```
    :  :   :   :::..::..|:..|:..:|: ..:|
196 YVISSCIGSFFAPCLIMILVVRIYQIAKRRTRVPPSRRGPDAVAAPPGG 245
        .           .           .
229 .QARFSSQSG....ETGEVQACPDKRYAMVLFRITSVFYILWLPYIIYFL 273
    |:.|.|.||            .:...:.||||||..:.|::..
346 LQGRGRSASGLPRRRAGAGGQNREKRFTFVLAVVIGVFVVCWFPFFFTYT 395
                 .           .           .
274 LESSTGHSNRFASFLTTWLAISNSFCNCVIYSLSNSVFQRGLKRLSGAMC 323
    |..:.          . :..:.|.|.|: .|:|:   :|
396 LTAVGCSVPRTLFKFFFWFGYCNSSLNPVIYTIFNHDFRRAFKKI...LC 442
                 .
324 TSCASQTT 331
    :  ....
443 RGDRKRIV 450
```

POLYNUCLEOTIDES ENCODING HUMAN G-PROTEIN COUPLED RECEPTOR HIBEF51

This invention relates to newly identified polynucleotides, polypeptides encoded by such polynucleotides, the use of such polynucleotides and polypeptides, as well as the production of such polynucleotides and polypeptides. More particularly, the polypeptide of the present invention is a human 7-transmembrane receptor. The transmembrane receptor is a G-protein coupled receptor. The invention also relates to inhibiting the action of such polypeptides.

It is well established that many medically significant biological processes are mediated by proteins participating in signal transduction pathways that involve G-proteins and/or second messengers, e.g., cAMP (Lefkowitz, Nature, 351:353–354 (1991)). Herein these proteins are referred to as proteins participating in pathways with G-proteins or PPG proteins. Some examples of these proteins include the GPC receptors, such as those for adrenergic agents and dopamine (Kobilka, B. K., et al., PNAS, 84:46–50 (1987); Kobilka, B. K., et al., Science, 238:650–656 (1987); Bunzow, J. R., et al., Nature, 336:783–787 (1988)), G-proteins themselves, effector proteins, e.g., phospholipase C, adenyl cyclase, and phosphodiesterase, and actuator proteins, e.g., protein kinase A and protein kinase C (Simon, M. I., et al., Science, 252:802–8 (1991)).

For example, in one form of signal transduction, the effect of hormone binding is activation of an enzyme, adenylate cyclase, inside the cell. Enzyme activation by hormones is dependent on the presence of the nucleotide GTP, and GTP also influences hormone binding. A G-protein connects the hormone receptors to adenylate cyclase. G-protein was shown to exchange GTP for bound GDP when activated by hormone receptors. The GTP-carrying form then binds to an activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors (GPRs) has been characterized as having seven putative transmembrane domains. The domains are believed to represent transmembrane α-helices connected by extracellular or cytoplasmic loops. G-protein coupled receptors include a wide range of biologically active receptors, such as hormone, viral, growth factor and neuroreceptors.

G-protein coupled receptors have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include calcitonin, adrenergic, endothelin, cAMP, adenosine, muscarinic, acetylcholine, serotonin, histamine, thrombin, kinin, follicle stimulating hormone, opsins and rhodopsins, odorant, cytomegalovirus receptors, etc.

Most GPRs have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. TM3 is also implicated in signal transduction.

Phosphorylation and lipidation (palmitylation or farnesylation) of cysteine residues can influence signal transduction of some GPRS. Most GPRs contain potential phosphorylation sites within the third cytoplasmic loop and/or the carboxy terminus. For several GPRs, such as the β-adrenoreceptor, phosphorylation by protein kinase A and/or specific receptor kinases mediates receptor desensitization.

The ligand binding sites of GPRs are believed to comprise a hydrophilic socket formed by several GPR transmembrane domains, which socket is surrounded by hydrophobic residues of the GPRs. The hydrophilic side of each GPR transmembrane helix is postulated to face inward and form the polar ligand binding site. TM3 has been implicated in several GPRs as having a ligand binding site, such as including the TM3 aspartate residue. Additionally, TM5 serines, a TM6 asparagine and TM6 or TM7 phenylalanines or tyrosines are also implicated in ligand binding.

GPRs can be intracellularly coupled by heterotrimeric G-proteins to various intracellular enzymes, ion channels and transporters (see, Johnson et al., Endoc., Rev., 10:317–331 (1989)). Different G-protein α-subunits preferentially stimulate particular effectors to modulate various biological functions in a cell. Phosphorylation of cytoplasmic residues of GPRs has been identified as an important mechanism for the regulation of G-protein coupling of some GPRs.

G-protein coupled receptors are found in numerous sites within a mammalian host, for example, dopamine is a critical neurotransmitter in the central nervous system and is a G-protein coupled receptor ligand.

In accordance with one aspect of the present invention, there are provided novel mature receptor polypeptides as well as biologically active and diagnostically or therapeutically useful fragments, analogs and derivatives thereof. The receptor polypeptides of the present invention are of human origin.

In accordance with another aspect of the present invention, there are provided isolated nucleic acid molecules encoding the receptor polypeptides of the present invention, including mRNAs, DNAs, cDNAs, genomic DNA as well as antisense analogs thereof and biologically active and diagnostically or therapeutically useful fragments thereof.

In accordance with a further aspect of the present invention, there are provided processes for producing such receptor polypeptides by recombinant techniques comprising culturing recombinant prokaryotic and/or eukaryotic host cells, containing nucleic acid sequences encoding the receptor polypeptides of the present invention, under conditions promoting expression of said polypeptides and subsequent recovery of said polypeptides.

In accordance with yet a further aspect of the present invention, there are provided antibodies against such receptor polypeptides.

In accordance with another aspect of the present invention there are provided methods of screening for compounds which bind to and activate or inhibit activation of the receptor polypeptides of the present invention.

In accordance with still another embodiment of the present invention there are provided processes of administering compounds to a host which bind to and activate the receptor polypeptide of the present invention which are useful in the prevention and/or treatment of upper respiratory conditions, for example, allergic rhinitis, hay fever, acute coryza and sinusitus, to promote uterine inhibition, to stimulate platelet aggregation, regulate lipid metabolism, and inhibit glucose-stimulated insulin release from the pancreas.

In accordance with another aspect of the present invention there is provided a method of administering the receptor polypeptides of the present invention via gene therapy to treat conditions related to underexpression of the polypeptides or underexpression of a ligand to the receptor polypeptide.

In accordance with still another embodiment of the present invention there are provided processes of administering compounds to a host which bind to and inhibit activation of the receptor polypeptides of the present invention which are useful in the prevention and/or treatment of hypertension and other myocardial disease and other diseases relating from vasoconstriction.

In accordance with yet another aspect of the present invention, there are provided nucleic acid probes comprising nucleic acid molecules of sufficient length to specifically hybridize to the polynucleotide sequences of the present invention.

In accordance with still another aspect of the present invention, there are provided diagnostic assays for detecting diseases related to mutations in the nucleic acid sequences encoding such polypeptides and for detecting an altered level of the soluble form of the receptor polypeptides.

In accordance with yet a further aspect of the present invention, there are provided processes for utilizing such receptor polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF DRAWINGS

The following drawings are illustrative of embodiments of the invention and are not meant to limit the scope of the invention as encompassed by the claims.

FIGS. 1A–E shows the cDNA sequence (SEQ ID NO:1) and the corresponding deduced amino acid sequence (SEQ ID NO:2) of the G-protein coupled receptor of the present invention. The standard one-letter abbreviation for amino acids is used. Sequencing was performed using a 373 Automated DNA sequencer (Applied Biosystems, Inc.).

FIGS. 2A–B illustrates an amino acid alignment of the G-protein coupled receptor of the present invention (top line of each comparative row, SEQ ID NO:2) and the human adrenergic $\alpha_2 A$ receptor (bottom line of each comparative row, SEQ ID NO:4).

In accordance with an aspect of the present invention, there is provided an isolated nucleic acid (polynucleotide) which encodes the mature polypeptide having the deduced amino acid sequence of FIGS. 1A–E or for the mature polypeptide encoded by the cDNA of the clone (HBEF51) deposited as ATCC Deposit No. 97182 with the ATCC, 12301 Parklawn Drive, Rockville, Md. 20852 on Jun. 1, 1995. Since the strain referred to is being maintained under the terms of the Budapest Treaty, it will be made available to a patent office signatory to the Budapest Treaty.

A polynucleotide encoding a polypeptide of the present invention may be found in skeletal muscle, heart and brain. The polynucleotide of this invention was discovered in a cDNA library derived from a human infant brain. It is structurally related to the G protein-coupled receptor family. It contains an open reading frame encoding a protein of 349 amino acid residues. The protein exhibits the highest degree of homology to a human $\alpha_2 A$ adrenergic receptor with 25.387% identity and 51.084% similarity over a 331 amino acid stretch.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A–E (SEQ ID NO:1) or that of the deposited clone or may be a different coding sequence which coding sequence, as a result of the redundancy or degeneracy of the genetic code, encodes the same mature polypeptide as the DNA of FIGS. 1A–E (SEQ ID NO:1) or the deposited cDNA.

The polynucleotide which encodes for the mature polypeptide of FIGS. 1A–E (SEQ ID NO:2) or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A–E (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A–E or the same mature polypeptide encoded by the cDNA of the deposited clone as well as variants of such polynucleotides which variants encode for a fragment, derivative or analog of the polypeptide of FIGS. 1A–E (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–E (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides may also encode for a soluble form of the receptor polypeptide which is the extracellular portion of the polypeptide which has been cleaved from the TM and intracellular domain of the full-length polypeptide of the present invention.

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length receptor gene may be used as a hybridization probe for a cDNA library to isolate the full length gene and to isolate other genes which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete receptor gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1A–E (SEQ ID NO:1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a receptor polypeptide which has the deduced amino acid sequence of FIGS. 1A–E (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIGS. 1A–E (SEQ ID NO:2) or that encoded by the deposited cDNA, means a polypeptide which either retains substantially the same biological function or activity as such polypeptide, i.e. functions as a receptor, or retains the ability to bind the ligand or the receptor even though the polypeptide does not function as an receptor, for example, a soluble form of the receptor. An analog includes an extracellular portion which can be cleaved from the transmembrane domain and intracellular portion to produce a soluble active peptide.

The polypeptide of the present invention may be a recombinant polypeptide, a natural polypeptide or a synthetic polypeptide, preferably a recombinant polypeptide.

The fragment, derivative or analog of the polypeptide of FIGS. 1A–E (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide which is employed for purification of the mature polypeptide, or (v) one in which a fragment of the polypeptide is soluble, i.e. not membrane bound, yet still binds ligands to the membrane bound receptor. Such fragments, derivatives and analogs are deemed to be within the scope of those skilled in the art from the teachings herein.

The polypeptides and polynucleotides of the present invention are preferably provided in an isolated form, and preferably are purified to homogeneity.

The polypeptides of the present invention include the polypeptide of SEQ ID NO:2 (in particular the mature polypeptide) as well as polypeptides which have at least 70% similarity (preferably at least a 70% identity) to the polypeptide of SEQ ID NO:2 and more preferably at least a 90% similarity (more preferably at least a 90% identity) to the polypeptide of SEQ ID NO:2 and still more preferably at least a 95% similarity (still more preferably at least a 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis, therefore, the fragments may be employed as intermediates for producing the full-length polypeptides. Fragments or portions of the polynucleotides of the present invention may be used to synthesize full-length polynucleotides of the present invention.

The term "gene" means the segment of DNA involved in producing a polypeptide chain; it includes regions preceding and following the coding region "leader and trailer" as well as intervening sequences (introns) between individual coding segments (exons).

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2(in particular the mature polypeptide) as well as polypeptides which have at least 70% similarity (preferably a 70% identity) to the polypeptide of SEQ ID NO:2and more preferably a 90% similarity (more preferably a 90% identity) to the polypeptide of SEQ ID NO:2and still more preferably a 95% similarity (still more preferably a 90% identity) to the polypeptide of SEQ ID NO:2and also include portions of such polypeptides with such portion of the polypeptide generally containing at least 30amino acids and more preferably at least 50amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella typhimurium; fungal cells, such as yeast; insect cells such as Drosophila and Spodoptera Sf9; animal cells such as CHO, COS or Bowes melanoma; adenovirus; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The receptor polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The polynucleotides and polypeptides of the present invention may be employed as research reagents and materials for discovery of treatments and diagnostics to human disease.

The receptor of the present invention may be employed in a process for screening for compounds which bind to and activate (agonists) or bind to and inhibit activation (antagonists) of the receptor polypeptide of the present invention.

In general, such screening procedures involve providing appropriate cells which express the receptor on the surface thereof. In particular, a polynucleotide encoding the receptor of the present invention is employed to transfect cells to thereby express the receptor. Such transfection may be accomplished by procedures as hereinabove described.

One such screening procedure involves the use of the melanophores which are transfected to express the receptor of the present invention. Such a screening technique is described in PCT WO 92/01810 published Feb. 6, 1992.

Thus, for example, such assay may be employed for screening for a receptor antagonist by contacting the melanophore cells which encode the receptor with both the receptor ligand and a compound to be screened. Inhibition of the signal generated by the ligand indicates that a compound is a potential antagonist for the receptor, i.e., inhibits activation of the receptor.

The screen may be employed for determining an agonist by contacting such cells with compounds to be screened and determining whether such compound generates a signal, i.e., activates the receptor.

Other screening techniques include the use of cells which express the receptor (for example, transfected CHO cells) in a system which measures extracellular pH changes caused by receptor activation, for example, as described in Science, volume 246, pages 181–296 (October 1989). For example, potential agonists or antagonists may be contacted with a cell which expresses the receptor and a second messenger response, e.g. signal transduction or pH changes, may be measured to determine whether the potential agonist or antagonist is effective.

Another such screening technique involves introducing RNA encoding the receptor into xenopus oocytes to transiently express the receptor. The receptor oocytes may then be contacted in the case of antagonist screening with the receptor ligand and a compound to be screened, followed by detection of inhibition of a calcium signal.

Another screening technique involves expressing the receptor in which the receptor is linked to a phospholipase C or D. As representative examples of such cells, there may be mentioned endothelial cells, smooth muscle cells, embryonic kidney cells, etc. The screening for an antagonist or agonist may be accomplished as hereinabove described by detecting activation of the receptor or inhibition of activation of the receptor from the phospholipase second signal.

Another method involves screening for compounds which inhibit activation of the receptor polypeptide of the present invention by determining inhibition of binding of labeled ligand to cells which have the receptor on the surface thereof. Such a method involves transfecting a eukaryotic cell with DNA encoding the receptor such that the cell expresses the receptor on its surface and contacting the cell with a potential antagonist in the presence of a labeled form of a known ligand. The ligand can be labeled, e.g., by radioactivity. The amount of labeled ligand bound to the receptors is measured, e.g., by measuring radioactivity of the receptors. If the potential antagonist binds to the receptor as determined by a reduction of labeled ligand which binds to the receptors, the binding of labeled ligand to the receptor is inhibited.

In general, antagonists for G-protein coupled receptors which are determined by screening procedures may be employed for a variety of therapeutic purposes. For example, such antagonists have been employed for treatment of hypertension, angina pectoris, myocardial infarction, ulcers, asthma, allergies, psychoses, depression, migraine, vomiting, stroke, eating disorders, migraine headaches, cancer and benign prostatic hypertrophy.

Agonists for G-protein coupled receptors are also useful for therapeutic purposes, such as the treatment of asthma, Parkinson's disease, acute heart failure, hypotension, urinary retention, and osteoporosis.

Examples of G-protein coupled receptor antagonists include an antibody, or in some cases an oligonucleotide, which binds to the G-protein coupled receptor but does not elicit a second messenger response such that the activity of the G-protein coupled receptor is prevented. Antibodies include anti-idiotypic antibodies which recognize unique determinants generally associated with the antigen-binding site of an antibody. Potential antagonists also include proteins which are closely related to the ligand of the G-protein coupled receptor, i.e. a fragment of the ligand, which have lost biological function and when binding to the G-protein coupled receptor, elicit no response.

A potential antagonist also includes an antisense construct prepared through the use of antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of G-protein coupled receptor. The antisense RNA oligonucleotide hybridizes to the mRNA in vivo and blocks translation of the mRNA molecule into the G-protein coupled receptor (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of G-protein coupled receptor.

Another potential antagonist is a small molecule which binds to the G-protein coupled receptor, making it inaccessible to ligands such that normal biological activity is prevented. Examples of small molecules include but are not limited to small peptides or peptide-like molecules.

Potential antagonists also include a soluble form of a G-protein coupled receptor, e.g. a fragment of the receptor, which binds to the ligand and prevents the ligand from interacting with membrane bound G-protein coupled receptors.

The G-protein coupled receptor and antagonists or agonists may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the topical, intravenous, intraperitoneal, intramuscular, subcutaneous, intranasal or intradermal routes. The pharmaceutical compositions are administered in an amount which is effective for treating and/or prophylaxis of the specific indication. In general, the pharmaceutical compositions will be administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The G-protein coupled receptor polypeptides and antagonists or agonists which are polypeptides, may be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

G-protein coupled receptors are ubiquitous in the mammalian host and are responsible for many biological functions, including many pathologies. Accordingly, it is desirous to find compounds which stimulate a G-protein coupled receptor and compounds which antagonize a G-protein coupled receptor.

This invention further provides a method of identifying compounds which specifically interact with, and bind to, the human G-protein coupled receptors on the surface of a cell which comprises contacting a mammalian cell comprising an isolated DNA molecule encoding the G-protein coupled receptor with a plurality of compounds, determining those which bind to the mammalian cell, and thereby identifying compounds which specifically interact with and bind to a human G-protein coupled receptor of the present invention.

This invention also provides a method of detecting expression of the G-protein coupled receptor on the surface of a cell by detecting the presence of mRNA coding for a G-protein coupled receptor which comprises obtaining total mRNA from the cell and contacting the mRNA so obtained with a nucleic acid probe comprising a nucleic acid molecule of at least 15 nucleotides capable of specifically hybridizing with a sequence included within the sequence of a nucleic acid molecule encoding a human G-protein coupled receptor under hybridizing conditions, detecting the presence of mRNA hybridized to the probe, and thereby detecting the expression of the G-protein coupled receptor by the cell.

This invention is also related to the use of the G-protein coupled receptor gene as part of a diagnostic assay for detecting diseases or susceptibility to diseases related to the presence of mutated G-protein coupled receptor genes. Such diseases are related to cell transformation, such as tumors and cancers.

Individuals carrying mutations in the human G-protein coupled receptor gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding the G-protein coupled receptor protein can be used to identify and analyze G-protein coupled receptor mutations. For example, deletions and insertions can be detected by a change in size of the amplified product in comparison to the normal genotype. Point mutations can be identified by hybridizing amplified DNA to radiolabeled G-protein coupled receptor RNA or alternatively, radiolabeled G-protein coupled receptor antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, U.S.A., 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of soluble forms of the receptor polypeptides of the present invention in various tissues. Assays used to detect levels of the soluble receptor polypeptides in a sample derived from a host are well known to those of skill in the art and include radioimmunoassays, competitive-binding assays, Western blot analysis and preferably as ELISA assay.

An ELISA assay initially comprises preparing an antibody specific to antigens of the G-protein coupled receptor polypeptides, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any G-protein coupled receptor proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to G-protein receptor proteins. Unattached reporter antibody is then washed out. Peroxidase substrates are then added to the dish and the amount of color developed in a given time period is a measurement of the amount of G-protein coupled receptor proteins present in a given volume of patient sample when compared against a standard curve.

The present invention also provides a method for determining whether a ligand not known to be capable of binding to a receptor can bind to such receptor which comprises contacting a mammalian cell which expresses a receptor with the ligand under conditions permitting binding of ligands to the receptor, detecting the presence of a ligand which binds to the receptor and thereby determining whether the ligand binds to the receptor. The systems hereinabove described for determining agonists and/or antagonists may also be employed for determining ligands which bind to the receptor.

This invention also provides a method of detecting expression of a receptor polypeptide of the present invention on the surface of a cell by detecting the presence of mRNA coding for the receptor which comprises obtaining total mRNA from the cell and contacting the mRNA so obtained with a nucleic acid probe comprising a nucleic acid molecule of at least 10 nucleotides capable of specifically hybridizing with a sequence included within the sequence of a nucleic acid molecule encoding the receptor under hybridizing conditions, detecting the presence of mRNA hybridized to the probe, and thereby detecting the expression of the receptor by the cell.

The present invention also provides a method for identifying receptors related to the receptor polypeptides of the present invention. These related receptors may be identified by homology to an receptor polypeptide of the present invention, by low stringency cross hybridization, or by identifying receptors that interact with related natural or synthetic ligands and or elicit similar behaviors after genetic or pharmacological blockade of the receptor polypeptides of the present invention.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process.

These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short 50 as or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 $\mu$g of approximately equimolar amounts of the DNA fragments to be ligated.

Unless otherwise stated, transformation was performed as described in the method of Graham, F. and Van der Eb, A., Virology, 52:456–457 (1973).

EXAMPLE 1
Bacterial Expression and Purification of G-protein Coupled Receptor The DNA sequence encoding the receptor, ATCC No. 97182 is initially amplified using PCR oligonucleotide primers corresponding to the 5' and sequences of the processed receptor protein (minus the signal peptide sequence) and the vector sequences 3' to the receptor gene. Additional nucleotides corresponding to receptor were added to the 5' and 3' sequences respectively. The 5' oligonucleotide primer has the sequence 5'-CGGAATTCCTCCATGAACTCCACCTTGGAT-3' (SEQ ID NO:5) contains a Eco RI restriction enzyme site followed by 18 nucleotides of receptor coding sequence starting from the presumed terminal amino acid of the processed protein codon. The 3' sequence 5'-CGGAAGCTTCGTCAGATATGACATCCATT-3' (SEQ ID NO:6) contains complementary sequences to HindIII site and is followed by 18 nucleotides of receptor. The restriction enzyme sites correspond to the restriction enzyme sites on the bacterial expression vector pQE-9. (Qiagen, Inc. 9259 Eton Avenue, Chatsworth, Calif. 91311). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 was then digested with Eco RI and HindIII. The amplified sequences were ligated into pQE-9 and were inserted in frame with the sequence encoding for the histidine tag and the RBS. The ligation mixture was then used to transform E. coli strain available from Qiagen under the trademark M15/rep 4 by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies were selected. Plasmid DNA was isolated and confirmed by restriction analysis.

Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized receptor was purified from this solution by chromatography on a Nickel-Chelate column under conditions that allow for tight binding by proteins containing the 6-His tag. Hochuli, E. et al., J. Chromatography 411:177–184 (1984). The receptor protein was eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

EXAMPLE 2
Expression of Recombinant Receptor in COS cells

The expression of plasmid, G-protein coupled receptor HA is derived from a vector pcDNAI/Amp (Invitrogen) containing: 1) SV40 origin of replication, 2) ampicillin resistance gene, 3) E.coli replication origin, 4) CMV promoter followed by a polylinker region, a SV40 intron and polyadenylation site. A DNA fragment encoding the entire receptor precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A. Cherenson, M. Connolly, and R. Lerner, 1984, Cell 37, 767). The infusion of HA tag to our target protein allows easy detection of the recombinant protein with an antibody that recognizes the HA epitope.

The plasmid construction strategy is described as follows: The DNA sequence encoding for the receptor, ATCC No. 97182, was constructed by PCR on the original EST cloned using two primers: the 5' primer (5'-GTCCAAGCTTGCCACCATGAACTCCACCTTGGAT-3') (SEQ ID NO:7) contains a HindIII site followed by 18 nucleotides of receptor coding sequence starting from the initiation codon; the 3' sequence 5'-CTAGCTCGAGTC-AAGCGTACTCTGGGACGTCGTATGGGTAGCAGAT-ATGACATCCATTAAG-3' (SEQ ID NO:8) contains complementary sequences to Xho I site, translation stop codon, HA tag and the last 18 nucleotides of the receptor coding sequence (not including the stop codon). Therefore, the PCR product contains a HindIII site, receptor coding sequence followed by HA tag fused in frame, a translation termination stop codon next to the HA tag, and an Xho I site. The PCR amplified DNA fragment and the vector, pcDNAI/Amp, were digested with HindIII and Xho I restriction enzyme and ligated. The ligation mixture was transformed into E. coli strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant receptor, COS cells were transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the receptor HA protein was detected by radiolabelling and immunoprecipitation method. (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). Both cell lysate and culture media were precipitated with a HA specific monoclonal antibody. Proteins precipitated were analyzed on 15% SDS-PAGE gels.

EXAMPLE 3
Cloning and expression of G-protein Coupled receptor using the baculovirus expression system The DNA sequence encoding the full length receptor protein, ATCC No. 97182, was amplified using PCR oligonucleotide primers corresponding to the 5' and 3' sequences of the gene:

The 5' primer has the sequence 5'-CGGGATCCCTCCATGAACTCCACCTTGGAT (SEQ ID NO:9) and contains a Bam HI restriction enzyme site (in bold) followed by 4 nucleotides resembling an efficient signal for the initiation of translation in eukaryotic cells (J. Mol. Biol. 1987, 196, 947–950, Kozak, M.), and just behind the first 18 nucleotides of the receptor gene (the initiation codon for translation "ATG" is underlined).

The 3' primer has the sequence 5'-CGGGATCCCGCTCAGATATGAGATCCATT-3' (SEQ ID NO:10) and contains the cleavage site for the restriction endonuclease Bam HI and 18 nucleotides complementary to the 3' non-translated sequence of the receptor gene. The amplified sequences were isolated from a 1% agarose gel using a commercially available kit ("Geneclean," BIO 101 Inc., La Jolla, Calif.). The fragment was then digested with the endonucleases Bam HI and then purified as described in Example 1. This fragment is designated F2.

The vector pRG1 (modification of pVL941 vector, discussed below) is used for the expression of the receptor protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases Bam HI. The polyadenylation site of the simian virus (SV)40 is used for efficient polyadenylation. For an easy selection of recombinant viruses the beta-galactosidase gene from E.coli is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid was digested with the restriction enzyme Bam HI and then dephosphorylated using calf intestinal phosphatase by procedures known in the art. The DNA was then isolated from a 1% agarose gel as described in Example 1. This vector DNA is designated V2.

Fragment F2 and the dephosphorylated plasmid V2 were ligated with T4 DNA ligase. E.coli HB101 cells were then transformed and bacteria identified that contained the plasmid (pBac receptor) with the receptor gene using the enzymes Bam HI. The sequence of the cloned fragment was confirmed by DNA sequencing.

5 μg of the plasmid pBac receptor were co-transfected with 1.0 μg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 μg of BaculoGold™ virus DNA and 5 μg of the plasmid pBac receptor were mixed in a sterile well of a microtiter plate containing 50 μl of serum free Grace's medium (Life Technologies Inc., Gaithersburg, Md). Afterwards 10 μl Lipofectin plus 90 μl Grace's medium were added, mixed and incubated for 15 minutes at room temperature. Then the transfection mixture was added drop wise to the Sf9 insect cells (ATCC CRL 1711) seeded in a 35 mm tissue culture plate with 1 ml Grace' medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution of the viruses was added to the cells, blue stained plaques were picked with the tip of an Eppendorf pipette. The agar containing the recombinant viruses was then resuspended in an Eppendorf tube containing 200 μl of Grace's medium. The agar was removed by a brief centrifugation and the supernatant containing the recombinant baculoviruses was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-receptor at a multiplicity of infection (MOI) of 2. Six hours later the medium was removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) were added. The cells were further incubated for 16 hours before they were harvested by centrifugation and the labelled proteins visualized by SDS-PAGE and autoradiography.

EXAMPLE 4

Expression pattern of G-protein Coupled receptor in human tissue

Northern blot analysis was carried out to examine the levels of expression of receptor in human tissues. Total cellular RNA samples were isolated with RNAzol™ B system (Biotecx Laboratories, Inc. 6023 South Loop East, Houston, Tex. 77033). About 10 μg of total RNA isolated from each human tissue specified was separated on 1% agarose gel and blotted onto a nylon filter. (Sambrook, Fritsch, and Maniatis, Molecular Cloning, Cold Spring Harbor Press, (1989)). The labeling reaction was done according to the Stratagene Prime-It kit with 50 ng DNA fragment. The labeled DNA was purified with a Select-G-50 column. (5 Prime-3 Prime, Inc. 5603 Arapahoe Road, Boulder, Colo. 80303). The filter was then hybridized with radioactive labeled full length receptor gene at 1,000,000 cpm/ml in 0.5M NaPO$_4$, pH 7.4 and 7% SDS overnight at 65° C. After wash twice at room temperature and twice at 60° C. with 0.5×SSC, 0.1% SDS, the filter was then exposed at −70° C. overnight with an intensifying screen. The message RNA for the receptor is abundant in skeletal muscle.

EXAMPLE 5

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer contains an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated nucleic acid comprising a polynucleotide selected from the group consisting of:
   (a) a polynucleotide encoding amino acids 1–349 of SEQ ID NO:2;
   (b) a polynucleotide encoding amino acids 2–349 of SEQ ID NO:2;
   (c) a polynucleotide encoding the amino acid sequence encoded by the cDNA clone contained in ATCC Deposit No. 97182;
   (d) the complement of (a);
   (e) the complement of (b);
   (f) the complement of (c); and
   (g) a polynucleotide encoding the mature polypeptide encoded by the cDNA clone contained in ATCC Deposit No. 97182.

2. The isolated nucleic acid of claim 1, wherein said polynucleotide is (a).

3. The isolated nucleic acid molecule of claim 2, which comprises nucleotides 832 to 1878 of SEQ ID NO:1.

4. The isolated nucleic acid of claim 1, wherein said polynucleotide is (b).

5. The isolated nucleic acid molecule of claim 4, which comprises nucleotides 835 to 1878 of SEQ ID NO:1.

6. The isolated nucleic acid of claim 1, wherein said polynucleotide is (c).

7. The isolated nucleic acid of claim 1, wherein said polynucleotide is (d).

8. The isolated nucleic acid of claim 1, wherein said polynucleotide is (e).

9. The isolated nucleic acid of claim 1, wherein said polynucleotide is (f).

10. The isolated nucleic acid of claim 1, wherein said polynucleotide is (g).

11. The isolated nucleic acid molecule of claim 1 which is DNA.

12. The isolated nucleic acid molecule of claim 1 which is RNA.

13. The isolated nucleic acid molecule of claim 1, wherein said polynucleotide is fused to a heterologous polynucleotide.

14. The isolated nucleic acid molecule of claim 13, wherein said heterologous polynucleotide encodes a heterologous polypeptide.

15. A vector comprising the isolated nucleic acid molecule of claim 1.

16. A host cell genetically engineered to comprise the isolated nucleic acid molecule of claim 1.

17. A host sell genetically engineered to comprise the isolated nucleic acid molecule of claim 1 operatively associated with a promoter.

18. A vector comprising a polynucleotide selected from the group consisting of;
 (a) a polynucleotide encoding amino acids 1–349 of SEQ ID NO:2;
 (b) a polynucleotide encoding amino acids 2–349 of SEQ ID NO:2;
 (c) a polynucleotide encoding amino acids sequence encoded by the cDNA clone contained in ATCC Deposit No. 97182; and
 (d) a polynucleotide encoding the mature polypeptide encoded by the cDNA clone contained in ATCC Deposit No. 97182;
wherein said polynucleotide is operatively associated with a promoter.

19. A host cell genetically engineered to comprise the vector of claim 18.

20. A method of producing a polypeptide comprising:
 (a) culturing the host cell of claim 19 under conditions such that said polypeptide is expressed; and
 (b) recovering said polypeptide.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 2764 base pairs
      (B) TYPE: nucleic acid
      (C) STRANDEDNESS:single
      (D) TOPOLOGY: linear (ii) MOLECULE TYPE: cDNA (xi) SEQUENCE DESCRIPTION: SEQ ID NO:1:

```
AATTACAGGT AACATTCTGA AATTGAACTA AACAGTAAAT TCTGTTGAAA TGTTTTCAAA      60

GAGGCAAAAT ATTATATTGG AATCAATGAA GAAAGTAAAT TATCTTGGCT AATTTTATTA     120

GTGGTAATTG TAGTGAAAGG TTTTCCTAAA TATTATAAGC AAATTCCTTT TCTCCCCCGT     180

CTCAAATGAA AGGAAATGGG GGTAAATTAA TCTGACTGTG ATTGGTTTTG TTTTATGCTG     240

ATCTTGAAAG CTTGATGTTG CTGCTGCTCC TCATACAGTA CAGATCAGTT GTGTGGGGTG     300

CTATTGAGGG TAGCCGTGAA TAGTGGTGCC AGTAGGGGTG GAGCGGGAGG GATGATGCCA     360

GCCTGAGCTA GCCAGGTTCT TTGATTAGGG CATTGGATGT GAAATGTAAA ATGCTCTCTC     420

CTTTTCTTCT ATCAGCTGTT CAGAGGAGAC TCATTACAAC TCCTGCTGAA GCTCCTAATC     480

TTCTTCCCTT CTCTTCTACC CTTTCCCCCT ACCCTCACTT GGCCTGAAGA CGTTCTCCCC     540

AGAGTTTACC TTGCTCCCCT GGTGCTATGT GTATGGTGAA CCTGGCACTA TGGCCGCGTC     600

TGGGACTGGC CAGACAACTG CTGCTGGCTC TCCTTATTCC AGGAAGGATT TAAAGGGGAA     660

TTGCACTGCA GGCAATGCAC CAGAGCAGCA GCATCAGGAG CTTGGGGAGT AAGGCTCCTC     720

TGGCATTATT ACACACATGC AAAGCTGACC GCAATGACAG CAGCTGCTTC TTTGAACTGT     780

TGGCAGCAGC CAAGCGGCAG CATGAAGTGA CAGATCACTC CTGAGCTCAA G ATG AAC     837
                                                         Met Asn
```

| | | | | | | | | | | | | | | | | |
|---|---|---|---|---|---|---|---|---|---|---|---|---|---|---|---|---|
| TCC | ACC | TTG | GAT | GGT | AAT | CAG | AGC | AGC | CAC | CCT | TTT | TGC | CTC | TTG | GCA | 885 |
| Ser | Thr | Leu | Asp | Gly | Asn | Gln | Ser | Ser | His | Pro | Phe | Cys | Leu | Leu | Ala | |
| | | | 5 | | | | | 10 | | | | | 15 | | | |
| TTT | GGC | TAT | TTG | GAA | ACT | GTC | AAT | TTT | TGC | CTT | TTG | GAA | GTA | TTG | ATT | 933 |
| Phe | Gly | Tyr | Leu | Glu | Thr | Val | Asn | Phe | Cys | Leu | Leu | Glu | Val | Leu | Ile | |
| | | 20 | | | | | 25 | | | | | 30 | | | | |
| ATT | GTC | TTT | CTA | ACT | GTA | TTG | ATT | ATT | TCT | GGC | AAC | ATC | ATT | GTG | ATT | 981 |
| Ile | Val | Phe | Leu | Thr | Val | Leu | Ile | Ile | Ser | Gly | Asn | Ile | Ile | Val | Ile | |
| 35 | | | | | 40 | | | | | 45 | | | | | 50 | |
| TTT | GTA | TTT | CAC | TGT | GCA | CCT | TTG | TTG | AAC | CAT | CAC | ACT | ACA | AGT | TAT | 1029 |
| Phe | Val | Phe | His | Cys | Ala | Pro | Leu | Leu | Asn | His | His | Thr | Thr | Ser | Tyr | |
| | | | | 55 | | | | | 60 | | | | | 65 | | |
| TTT | ATC | CAG | ACT | ATG | GCA | TAT | GCT | GAC | CTT | TTT | GTT | GGG | GTG | AGC | TGC | 1077 |
| Phe | Ile | Gln | Thr | Met | Ala | Tyr | Ala | Asp | Leu | Phe | Val | Gly | Val | Ser | Cys | |
| | | | | 70 | | | | | 75 | | | | | 80 | | |
| GTG | GTC | CCT | TCT | TTA | TCA | CTC | CTC | CAT | CAC | CCC | CTT | CCA | GTA | GAG | GAG | 1125 |
| Val | Val | Pro | Ser | Leu | Ser | Leu | Leu | His | His | Pro | Leu | Pro | Val | Glu | Glu | |
| | | | | 85 | | | | | 90 | | | | | 95 | | |
| TCC | TTG | ACT | TGC | CAG | ATA | TTT | GGT | TTT | GTA | GTA | TCA | GTT | CTG | AAG | AGC | 1173 |
| Ser | Leu | Thr | Cys | Gln | Ile | Phe | Gly | Phe | Val | Val | Ser | Val | Leu | Lys | Ser | |
| | | | 100 | | | | | 105 | | | | | 110 | | | |
| GTC | TCC | ATG | GCT | TCT | CTG | GCC | TGT | ATC | AGC | ATT | GAT | AGA | TAC | ATT | GCC | 1221 |
| Val | Ser | Met | Ala | Ser | Leu | Ala | Cys | Ile | Ser | Ile | Asp | Arg | Tyr | Ile | Ala | |
| 115 | | | | | 120 | | | | | 125 | | | | | 130 | |
| ATT | ACT | AAA | CCT | TTA | ACC | TAT | AAT | ACT | CTG | GTT | ACA | CCC | TGG | AGA | CTA | 1269 |
| Ile | Thr | Lys | Pro | Leu | Thr | Tyr | Asn | Thr | Leu | Val | Thr | Pro | Trp | Arg | Leu | |
| | | | | 135 | | | | | 140 | | | | | 145 | | |
| CGC | CTG | TGT | ATT | TTC | CTG | ATT | TGG | CTA | TAC | TCG | ACC | CTG | GTC | TTC | CTG | 1317 |
| Arg | Leu | Cys | Ile | Phe | Leu | Ile | Trp | Leu | Tyr | Ser | Thr | Leu | Val | Phe | Leu | |
| | | | | 150 | | | | | 155 | | | | | 160 | | |
| CCT | TCC | TTT | TTC | CAC | TGG | GGC | AAA | CCT | GGA | TAT | CAT | GGA | GAT | GTG | TTT | 1365 |
| Pro | Ser | Phe | Phe | His | Trp | Gly | Lys | Pro | Gly | Tyr | His | Gly | Asp | Val | Phe | |
| | | 165 | | | | | 170 | | | | | 175 | | | | |
| CAG | TGG | TGT | GCG | GAG | TCC | TGG | CAC | ACC | GAC | TCC | TAC | TTC | ACC | CTG | TTC | 1413 |
| Gln | Trp | Cys | Ala | Glu | Ser | Trp | His | Thr | Asp | Ser | Tyr | Phe | Thr | Leu | Phe | |
| | | | 180 | | | | | 185 | | | | | 190 | | | |
| ATC | GTG | ATG | ATG | TTA | TAT | GCC | CCA | GCA | GCC | CTT | ATT | GTC | TGC | TTC | ACC | 1461 |
| Ile | Val | Met | Met | Leu | Tyr | Ala | Pro | Ala | Ala | Leu | Ile | Val | Cys | Phe | Thr | |
| 195 | | | | | 200 | | | | | 205 | | | | | 210 | |
| TAT | TTC | AAC | ATC | TTC | CGC | ATC | TGC | CAA | CAG | CAC | ACA | AAG | GAT | ATC | AGC | 1509 |
| Tyr | Phe | Asn | Ile | Phe | Arg | Ile | Cys | Gln | Gln | His | Thr | Lys | Asp | Ile | Ser | |
| | | | | 215 | | | | | 220 | | | | | 225 | | |
| GAA | AGG | CAA | GCC | CGC | TTC | AGC | AGC | CAG | AGT | GGG | GAG | ACT | GGG | GAA | GTG | 1557 |
| Glu | Arg | Gln | Ala | Arg | Phe | Ser | Ser | Gln | Ser | Gly | Glu | Thr | Gly | Glu | Val | |
| | | | 230 | | | | | 235 | | | | | 240 | | | |
| CAG | GCC | TGT | CCT | GAT | AAG | CGC | TAT | GCC | ATG | GTC | CTG | TTT | CGA | ATC | ACT | 1605 |
| Gln | Ala | Cys | Pro | Asp | Lys | Arg | Tyr | Ala | Met | Val | Leu | Phe | Arg | Ile | Thr | |
| | | 245 | | | | | 250 | | | | | 255 | | | | |
| AGT | GTA | TTT | TAC | ATC | CTC | TGG | TTG | CCA | TAT | ATC | ATC | TAC | TTC | TTG | TTG | 1653 |
| Ser | Val | Phe | Tyr | Ile | Leu | Trp | Leu | Pro | Tyr | Ile | Ile | Tyr | Phe | Leu | Leu | |
| | | 260 | | | | | 265 | | | | | 270 | | | | |
| GAA | AGC | TCC | ACT | GGC | CAC | AGC | AAC | CGC | TTC | GCA | TCC | TTC | TTG | ACC | ACC | 1701 |
| Glu | Ser | Ser | Thr | Gly | His | Ser | Asn | Arg | Phe | Ala | Ser | Phe | Leu | Thr | Thr | |
| 275 | | | | | 280 | | | | | 285 | | | | | 290 | |
| TGG | CTT | GCT | ATT | AGT | AAC | AGT | TTC | TGC | AAC | TGT | GTA | ATT | TAT | AGT | CTC | 1749 |
| Trp | Leu | Ala | Ile | Ser | Asn | Ser | Phe | Cys | Asn | Cys | Val | Ile | Tyr | Ser | Leu | |
| | | | | 295 | | | | | 300 | | | | | 305 | | |
| TCC | AAC | AGT | GTA | TTC | CAA | AGA | GGA | CTA | AAG | CGC | CTC | TCA | GGG | GCT | ATG | 1797 |
| Ser | Asn | Ser | Val | Phe | Gln | Arg | Gly | Leu | Lys | Arg | Leu | Ser | Gly | Ala | Met | |
| | | | 310 | | | | | 315 | | | | | 320 | | | |

```
TGT ACT TCT TGT GCA AGT CAG ACT ACA GCC AAC GAC CCT TAC ACA GTT     1845
Cys Thr Ser Cys Ala Ser Gln Thr Thr Ala Asn Asp Pro Tyr Thr Val
            325                 330                 335

AGA AGC AAA GGC CCT CTT AAT GGA TGT CAT ATC TGAAGTGGCT CAGTTACGGG   1898
Arg Ser Lys Gly Pro Leu Asn Gly Cys His Ile
340                 345

GTTCCCGTGT GTGTGTGTGT GTGTGTGTGT GTGTGTGTGT ATTTTATCTC TAAGTATTCC   1958

TAATTCACTA GGAAATCTGG GACAGAATAC TTTGACTCTA AACAATAGCA TACAAATTAT   2018

TCGTATGGAT ACCTTCTAAG TTTGTAGAAA TGGTTTTCCC AAGTGCTTGT GAATTAGAAG   2078

ACTCAAGATC ATGAAGACAA ATTGCTCTTG CTCTCAATTT TGAAATGTC TTGGAAATGA    2138

CTACAGTTCT CAGATTTAAA ATGAATAAAG CCATATCTAA CACCTCTTTC CAGCTGGCAT   2198

GACTGAACCT GAGTGTGAAA AGCGTCAGCA TTTTAAAAAG TCATCACTTT CTTGTCACTT   2258

TCTGGGCTCT TTCCAGCTAT TTGGGCGTCA TATGCAATTG ATTTCTTCTA ACGGAATAGT   2318

AAAATATAAA TGAAAAGGTT TTAGAAATTA CTTTTTATGT ATGCCAAAGC ATAACTACAC   2378

TGCAAGTTTC AACACTGTCA TTTAGAAAGC CAAATGTTCT GTGTTTTATT CTCTTGAGAG   2438

AATTCTCAGT AGGGTGAATA ATGTGAACAC ATAAACATTA ATTTTAGAAT TTACAGTGA    2498

ACCATGAAGC AAAAGTGCAA TCAAATTATA CAATTTATGA AAAACTGAGC TACTTTTTGT   2558

GCCATGCTTC ACAGAGATCT AAAGATATGT GTGCGTAGAA GTAATCGTGT AGTACTTTTG   2618

CCCATGCCTT TGTGTTATGT CTATATTTAG AATATCTGAA TTGTTAGATT TCTCTTTTAC   2678

AGCAAAATGT GCTTAAGCTA AAAAGTAATT CAGGGAATTC GATATCAAGC TTATCGATAC   2738

CGTCGACCTC GAGGGGGGGC CCGGTA                                        2764

(2) INFORMATION FOR SEQ ID NO:2:

(i) SEQUENCE CHARACTERISTICS:
        (A) LENGTH: 349 amino acids
        (B) TYPE: amino acid
        (D) TOPOLOGY: Linear (ii) MOLECULE TYPE: protein (xi) SEQUENCE DESCRIPTION: SEQ ID NO:2:

Met Asn Ser Thr Leu Asp Gly Asn Gln Ser Ser His Pro Phe Cys Leu
                 5                  10                  15

Leu Ala Phe Gly Tyr Leu Glu Thr Val Asn Phe Cys Leu Leu Glu Val
             20                  25                  30

Leu Ile Ile Val Phe Leu Thr Val Leu Ile Ile Ser Gly Asn Ile Ile
         35                  40                  45

Val Ile Phe Val Phe His Cys Ala Pro Leu Leu Asn His His Thr Thr
     50                  55                  60

Ser Tyr Phe Ile Gln Thr Met Ala Tyr Ala Asp Leu Phe Val Gly Val
 65                  70                  75                  80

Ser Cys Val Val Pro Ser Leu Ser Leu Leu His His Pro Leu Pro Val
                 85                  90                  95

Glu Glu Ser Leu Thr Cys Gln Ile Phe Gly Phe Val Val Ser Val Leu
            100                 105                 110

Lys Ser Val Ser Met Ala Ser Leu Ala Cys Ile Ser Ile Asp Arg Tyr
        115                 120                 125

Ile Ala Ile Thr Lys Pro Leu Thr Tyr Asn Thr Leu Val Thr Pro Trp
    130                 135                 140

Arg Leu Arg Leu Cys Ile Phe Leu Ile Trp Leu Tyr Ser Thr Leu Val
145                 150                 155                 160
```

```
Phe Leu Pro Ser Phe Phe His Trp Gly Lys Pro Gly Tyr His Gly Asp
            165                 170                 175

Val Phe Gln Trp Cys Ala Glu Ser Trp His Thr Asp Ser Tyr Phe Thr
            180                 185                 190

Leu Phe Ile Val Met Met Leu Tyr Ala Pro Ala Ala Leu Ile Val Cys
            195                 200                 205

Phe Thr Tyr Phe Asn Ile Phe Arg Ile Cys Gln Gln His Thr Lys Asp
            210                 215                 220

Ile Ser Glu Arg Gln Ala Arg Phe Ser Gln Ser Gly Glu Thr Gly
225                 230                 235                 240

Glu Val Gln Ala Cys Pro Asp Lys Arg Tyr Ala Met Val Leu Phe Arg
            245                 250                 255

Ile Thr Ser Val Phe Tyr Ile Leu Trp Leu Pro Tyr Ile Ile Tyr Phe
            260                 265                 270

Leu Leu Glu Ser Ser Thr Gly His Ser Asn Arg Phe Ala Ser Phe Leu
            275                 280                 285

Thr Thr Trp Leu Ala Ile Ser Asn Ser Phe Cys Asn Cys Val Ile Tyr
            290                 295                 300

Ser Leu Ser Asn Ser Val Phe Gln Arg Gly Leu Lys Arg Leu Ser Gly
305                 310                 315                 320

Ala Met Cys Thr Ser Cys Ala Ser Gln Thr Thr Ala Asn Asp Pro Tyr
            325                 330                 335

Thr Val Arg Ser Lys Gly Pro Leu Asn Gly Cys His Ile
            340                 345

(2) INFORMATION FOR SEQ ID NO:3:

(i) SEQUENCE CHARACTERISTICS:
        (A) LENGTH: 358 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:3:

Met Asn Ser Thr Leu Xaa Asp Gly Asn Gln Ser Ser His Pro Phe Cys
              5                  10                  15

Leu Leu Ala Phe Gly Tyr Leu Glu Thr Val Asn Phe Cys Leu Leu Glu
             20                  25                  30

Val Leu Ile Ile Val Xaa Xaa Xaa Phe Leu Thr Val Leu Ile Ile
             35                  40                  45

Ser Gly Asn Ile Ile Val Ile Phe Val Phe His Cys Ala Pro Leu Leu
 50                  55                  60

Asn His His Thr Thr Ser Tyr Phe Ile Gln Thr Met Ala Tyr Ala Asp
 65                  70                  75                  80

Leu Phe Val Gly Val Ser Cys Val Val Pro Ser Leu Ser Leu Leu His
             85                  90                  95

His Pro Leu Pro Xaa Xaa Val Glu Glu Ser Leu Thr Cys Gln Ile Phe
            100                 105                 110

Gly Phe Val Val Ser Val Leu Lys Ser Val Ser Met Ala Ser Leu Ala
            115                 120                 125

Cys Ile Ser Ile Asp Arg Tyr Ile Ala Ile Thr Lys Pro Leu Thr Tyr
            130                 135                 140

Asn Thr Leu Val Thr Pro Trp Arg Leu Arg Leu Cys Ile Phe Leu Ile
145                 150                 155                 160
```

```
Trp Leu Tyr Ser Thr Leu Val Phe Leu Pro Ser Phe His Trp Gly
            165                 170                 175

Lys Pro Gly Tyr His Gly Asp Val Phe Gln Trp Cys Ala Glu Ser Trp
            180                 185                 190

Xaa Xaa Xaa His Thr Asp Ser Tyr Phe Thr Leu Phe Ile Val Met Met
            195                 200                 205

Leu Tyr Ala Pro Ala Ala Leu Ile Val Cys Phe Thr Tyr Phe Asn Ile
210                 215                 220

Phe Arg Ile Cys Gln Gln His Thr Lys Asp Ile Ser Glu Arg Xaa Xaa
225                 230                 235                 240

Xaa Xaa Xaa Xaa Xaa Xaa Xaa Xaa Xaa Gln Ala Arg Phe Ser
            245                 250                 255

Ser Gln Ser Gly Xaa Xaa Xaa Xaa Glu Thr Gly Glu Val Gln Ala Cys
            260                 265                 270

Pro Asp Lys Arg Tyr Ala Met Val Leu Phe Arg Ile Thr Ser Val Phe
            275                 280                 285

Tyr Ile Leu Trp Leu Pro Tyr Ile Ile Tyr Phe Leu Leu Glu Ser Ser
290                 295                 300

Thr Gly His Ser Asn Arg Phe Ala Ser Phe Leu Thr Thr Trp Leu Ala
305                 310                 315                 320

Ile Ser Asn Ser Phe Cys Asn Cys Val Ile Tyr Ser Leu Ser Asn Ser
            325                 330                 335

Val Phe Gln Arg Gly Leu Lys Arg Leu Ser Gly Ala Met Cys Thr Ser
            340                 345                 350

Cys Ala Ser Gln Thr Thr
            355

(2) INFORMATION FOR SEQ ID NO:4:

(i) SEQUENCE CHARACTERISTICS:
        (A) LENGTH: 358 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:4:

Met Gly Ser Leu Gln Pro Asp Ala Gly Asn Ala Ser Trp Asn Gly Thr
                5                  10                  15

Glu Ala Pro Gly Gly Gly Ala Arg Ala Thr Pro Tyr Ser Leu Gln Val
            20                  25                  30

Thr Leu Thr Leu Val Cys Leu Ala Gly Leu Leu Met Leu Leu Thr Val
            35                  40                  45

Phe Gly Asn Val Leu Val Ile Ile Ala Val Phe Thr Ser Arg Ala Leu
50                  55                  60

Lys Ala Pro Gln Asn Leu Phe Leu Val Xaa Ser Leu Ala Ser Ala Asp
65                  70                  75                  80

Ile Leu Val Ala Xaa Xaa Thr Leu Val Ile Pro Phe Ser Leu Ala Asn
            85                  90                  95

Glu Val Met Gly Tyr Trp Tyr Phe Gly Lys Ala Trp Cys Glu Ile Tyr
            100                 105                 110

Leu Ala Leu Asp Val Leu Phe Cys Thr Ser Ser Ile Val His Leu Cys
            115                 120                 125

Ala Ile Ser Leu Asp Arg Tyr Trp Ser Ile Thr Gln Ala Ile Glu Tyr
            130                 135                 140
```

```
Asn Leu Lys Arg Thr Pro Arg Ile Lys Ala Ile Ile Thr Val
145                 150                 155                 160

Trp Val Ile Ser Ala Val Ile Ser Phe Pro Pro Leu Ile Ser Ile Glu
                165                 170                 175

Lys Lys Gly Xaa Xaa Gly Gly Gly Pro Gln Pro Ala Glu Pro Arg
                180                 185                 190

Cys Glu Ile Asn Asp Gln Lys Trp Tyr Val Ile Ser Ser Cys Ile Gly
                195                 200                 205

Ser Phe Phe Ala Pro Cys Leu Ile Met Ile Leu Val Tyr Val Arg Ile
                210                 215                 220

Tyr Gln Ile Ala Lys Arg Arg Thr Arg Val Pro Pro Ser Arg Arg Gly
225                 230                 235                 240

Pro Asp Ala Val Ala Ala Pro Pro Gly Gly Leu Gln Gly Arg Gly Arg
                245                 250                 255

Ser Ala Ser Gly Leu Pro Arg Arg Ala Gly Ala Gly Gly Gln Asn
                260                 265                 270

Arg Glu Lys Arg Phe Thr Phe Val Leu Ala Val Val Ile Gly Val Phe
                275                 280                 285

Val Val Cys Trp Phe Pro Phe Phe Thr Tyr Thr Leu Thr Ala Val
                290                 295                 300

Gly Cys Ser Val Pro Arg Thr Leu Phe Lys Phe Phe Trp Phe Gly
305                 310                 315                 320

Tyr Cys Asn Ser Ser Leu Asn Pro Val Ile Tyr Thr Ile Phe Asn His
                325                 330                 335

Asp Phe Arg Arg Ala Phe Lys Lys Ile Xaa Xaa Xaa Leu Cys Arg Gly
                340                 345                 350

Asp Arg Lys Arg Ile Val
                355

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CGGAATTCCT CCATGAACTC CACCTTGGAT                                              30

(2) INFORMATION FOR SEQ ID NO:6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CGGAAGCTTC GTCAGATATG ACATCCATT                                               29

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO:7:

GTCCAAGCTT GCCACCATGA ACTCCACCTT GGAT            34

(2) INFORMATION FOR SEQ ID NO:8:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CTAGCTCGAG TCAAGCGTAC TCTGGGACGT CGTATGGGTA GCAGATATGA CATCCATTAA            60

G            61

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

CGGGATCCCT CCATGAACTC CACCTTGGAT            30

(2) INFORMATION FOR SEQ ID NO:10:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CGGGATCCCG CTCAGATATG AGATCCATT            29